United States Patent [19]

Nikfar et al.

[11] Patent Number: 5,506,248
[45] Date of Patent: Apr. 9, 1996

[54] PHARMACEUTICAL COMPOSITIONS HAVING GOOD DISSOLUTION PROPERTIES

[75] Inventors: Faranak Nikfar, Bridgewater, N.J.; Abu T. M. Serajuddin, Flushing, N.Y.; Robert L. Jerzewski, Belle Mead; Nemichand B. Jain, Cranbury, both of N.J.

[73] Assignee: Bristol-Myers Squibb Company, Princeton, N.J.

[21] Appl. No.: 445,623

[22] Filed: May 22, 1995

Related U.S. Application Data

[63] Continuation-in-part of Ser. No. 257,149, Jun. 15, 1994, abandoned, which is a continuation-in-part of Ser. No. 100,802, Aug. 2, 1993, abandoned.

[51] Int. Cl.$^6$ ..................................................... A61K 31/42
[52] U.S. Cl. ................................................................ 514/374
[58] Field of Search ........................................... 514/374

[56] References Cited

U.S. PATENT DOCUMENTS 5,030,447  7/1991  Joshe et al. ............................ 514/548
5,100,889  3/1992  Misra et al. ............................ 514/374
5,180,589  1/1993  Joshi et al. ............................ 514/548

OTHER PUBLICATIONS

Remington's Pharmaceutical Sciences, 16th edition (1980) pp. 1555–1557.
The Handbook of Pharmaceutical Excipients © 1986 by APL A, pp. 26–29.

*Primary Examiner*—Raymond Henley, III
*Attorney, Agent, or Firm*—Burton Rodney

[57] ABSTRACT

An ifetroban composition is provided which has good dissolution properties even on aging, when dispersed in water has a pH of at least 7 and includes a salt of ifetroban, one or more basifying agents, such as magnesium oxide or calcium carbonate, and where in tablet form includes one or more fillers such as mannitol and/or microcrystalline cellulose, one or more disintegrating agents such as crospovidone, one or more lubricants such as magnesium stearate, optionally one or more glidants such as colloidal silicon dioxide, one or more binders such as pregelatinized starch (dry binder) or polyvinyl-pyrrolidone (wet binder) and optionally a film coating containing a film former such as hydroxypropyl cellulose and a plasticizer such as 1,2,3-propanetriol triacetate.

22 Claims, No Drawings

5,506,248

PHARMACEUTICAL COMPOSITIONS HAVING GOOD DISSOLUTION PROPERTIES

REFERENCE TO OTHER APPLICATIONS

This is a continuation-in-part of application Ser. No. 08/257,149 filed Jun. 15, 1994 now abandoned, which is a continuation-in-part of application Ser. No. 08/100,802, filed Aug. 2, 1993, now abandoned.

FIELD OF THE INVENTION

The present invention relates to a pharmaceutical composition, preferably in the form of a tablet or capsule, which includes as a medicament, a salt form of a weakly acidic drug, such as the sodium salt of BMS 180,291, which composition has good dissolution properties even on aging.

BACKGROUND OF THE INVENTION

Solubility of a drug is important with respect to drug dissolution rate from a solid dosage form and subsequent bioavailability for systemic absorption.

Where the free acid form of weakly acidic drugs have poor water-solubility, it has been the practice to employ such drugs in the form of their water-soluble salts. The water-soluble salts will generally have good dissolution properties and acceptable bioavailability characteristics.

BMS 180,291, a thromboxane $A_2$ receptor antagonist, disclosed in U.S. Pat. No. 5,100,889 to Misra et al, has the formula

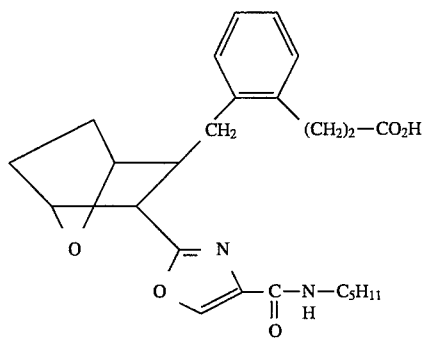

and the name [1S-(1α, 2α,3α,4α)]-2-[[3-[4-[(pentylamino)carbonyl] -2-oxazolyl]-7-oxabicyclo[2.2.1]hept- 2-yl] methyl]benzenepropanoic acid or a pharmaceutically acceptable salt thereof such as its sodium salt, potassium salt, calcium salt or magnesium salt.

For matter of convenience, BMS 180,291 will hereinafter be referred to as "ifetroban".

In its free acid form, ifetroban is poorly water-soluble (ca. 7 mcg/mL). The sodium salt of ifetroban is freely soluble in water (> 450 mg/mL) with excellent chemical and physical stability. Initially, capsule and tablet compositions of the sodium salt of ifetroban exhibit good chemical stability and rapid dissolution rate. However, upon storage for two weeks at 30° C., the dissolution rate of these compositions slow down dramatically. This is indeed surprising in view of the excellent chemical stability and high water-solubility of the sodium salt of ifetroban. In fact, it has been found that the sodium salt of ifetroban upon aging, undergoes an acid-base reaction resulting in formation of the free acid form of ifetroban which results in the dissolution rate slowdown.

DESCRIPTION OF THE INVENTION

In accordance with the present invention, a pharmaceutical composition is provided which has excellent dissolution properties after aging though it may include a medicament which even in its water-soluble salt form may have poor dissolution properties upon aging.

The pharmaceutical composition of the invention, which is preferably in the form of a tablet or capsule, includes a medicament in the form of a water-soluble salt, which could under acidic or near neutral conditions convert to its poorly water-soluble free acid form, such as an alkali metal salt or alkaline earth metal salt of ifetroban, such as ifetroban sodium, potassium, calcium or magnesium salt. The composition of the invention will also include one or more basifying agents such as magnesium oxide or calcium carbonate, to impart a pH to an aqueous dispersion of the composition of at least 7. In addition, the composition of the invention may include one or more fillers, such as mannitol and/or microcrystalline cellulose, and one or more lubricants such as magnesium stearate.

The composition of the invention in the form of a tablet will also contain one or more tablet disintegrating agents, such as croscarmellose sodium, and optionally one or more binders, such as microcrystalline cellulose (dry binder) polyvinylpyrrolidone (wet binder), optionally one or more glidants or flow aids such as colloidal silica, and optionally a film coating as described hereinafter.

The composition of the invention in the form of a capsule will optionally contain one or more disintegrants such as croscarmellose sodium and optionally one or more glidants or flow aids such as colloidal silica.

It has been found that by maintaining the composition of the invention at a pH of at least 7 (when dispersed in water) by using an appropriate basifying agent to prevent the acid-base reaction of the ifetroban salt, the salt form is maintained (formation of the free acid is inhibited) and rapid dissolution rate of the dosage form of the composition is achieved even after aging.

In addition, in accordance with the present invention, a method is provided for maintaining good dissolution properties of a pharmaceutical composition which contains a salt of ifetroban, such as an alkali metal salt like sodium, potassium or lithium salt, by inhibiting conversion of the salt to its corresponding free acid, wherein one or more basifying agents is employed with the salt of ifetroban, to impart a desired pH of at least 7 (to an aqueous dispersion thereof).

The pH of the composition may be determined by measuring the pH of the supernatant of a 70% w/w slurry of the composition in water.

The invention is particularly adapted to pharmaceutical compositions containing a salt of ifetroban as the medicament which will be present in an amount within the range of from about 1 to about 60%, and preferably from about 5 to about 50% by weight of the composition.

The salts of ifetroban suitable for use herein include alkali metal salts such as the sodium salt, potassium salt or lithium salt, alkaline earth metal salts such as the calcium salt or magnesium salt, amine salts such as the dicycloamine salt, the adamantane amine salt, amino acid salts, such as arginine and lysine salts, as well as any of the salts disclosed in U.S. Pat. No. 5,100,889 which is incorporated herein by reference.

To ensure acceptable dissolution rate of the composition of the invention upon aging, the composition of the invention will include a basifying agent which will raise the pH of an aqueous dispersion of the composition to at least 7 up to about 12, and preferably to a pH of at least 8 and more preferably to a pH of from about 9 to about 11. The basifying agent will be present in an amount within the range of from about 0.2 to about 75% by weight and preferably from about 1 to about 10% by weight of the composition. Examples of basifying agents which are suitable for use herein include, but are not limited to magnesium oxide, aluminum oxide, ammonium hydroxide, magaldrate, an alkali metal salt or alkaline earth metal salt, such as sodium bicarbonate, calcium carbonate or sodium citrate, an alkali metal hydroxide such as sodium hydroxide, potassium hydroxide or lithium hydroxide, or an alkaline earth metal hydroxide such as calcium hydroxide or magnesium hydroxide, with magnesium oxide or calcium carbonate being preferred.

The composition of the invention may also include one or more fillers or excipients in an amount within the range of from about 5 to about 95% by weight, and preferably from about 10 to about 90% by weight, such as lactose, dicalcium phosphate dihydrate, sucrose, corn starch, modified corn starch, mannitol, sorbitol, maltodextrin, calcium sulfate, inorganic salts such as calcium carbonate and/or cellulose derivatives such as wood cellulose and microcrystalline cellulose.

Where the composition of the invention is in the form of a tablet, it will include one or more tablet disintegrants in an amount within the range of from about 0.5 to about 10% and preferably from about 2 to about 8% by weight of the composition such as croscarmellose sodium, crospovidone, sodium starch glycolate, pregelatinized starch or corn starch or microcrystalline cellulose as well as one or more tableting lubricants in an amount within the range of from about 0.2 to about 8% and preferably from about 0.5 to about 2% by weight of the composition, such as magnesium stearate, stearic acid, palmitic acid, sodium stearyl fumarate, calcium stearate, talc, carnauba wax and the like.

The tablet of the invention will optionally include one or more binders which will be present in addition to or in lieu of the fillers in an amount within the range of from about 1 to about 35% and preferably from about 2 to about 20% by weight of the composition. Examples of such binders which are suitable for use herein include povidone (wet binder) (molecular weight ranging from about 5000 to about 80,000 and preferably about 30,000), pregelatinized starch (dry binder), starches such as corn starch, modified corn starch, sugars, hydroxypropyl methyl cellulose, gum acacia and the like, as well as a wax binder in finely powdered form (less than 500 microns) such as carnauba wax, paraffin, spermaceti, polyethylenes or microcrystalline wax.

Other conventional ingredients which may optionally be present in the tablet of the invention include preservatives, stabilizers, anti-adherents or silica flow conditioners or glidants, such as Syloid brand silicon dioxide as well as FD&C colors such as ferric oxides.

Tablets of the invention may also include a coating layer which may comprise from 0 to about 15%, preferably from about 0.5 to about 12%, and more preferably from about 2 to about 4% by weight of the coated tablet composition. The coating layer which is applied over the tablet core may comprise any conventional coating formulations and will include one or more film-formers or binders, such as a hydrophilic polymer like hydroxypropylmethyl cellulose, methylcellulose, hydroxypropyl cellulose, sodium carboxymethyl cellulose, and/or a hydrophobic polymer like ethyl cellulose, cellulose acetate, polyvinyl alcohol-maleic anhydride copolymers, acrylic acid polymers and the like; and one or more plasticizers, such as 1,2,3-propanetriol triacetate, triethyl citrate, tributyl citrate, diethyl phthalate, castor oil, polyethylene glycol and the like. Both core tablets as well as coating formulations may contain aluminum lakes or iron oxides to provide color.

The film-formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the colorant such as ferric oxides, aluminum lakes of FD & C dyes, titanium dioxide and the like will be applied together with the film former, plasticizer and solvent compositions.

Alternatively, film coating systems such as OPADRY™, Pharmacoat 606™ with Chromakote™ or other available systems may be used. OPADRY™ is formed of hydroxypropylmethyl cellulose, polyethylene glycol, titanium dioxide and polysorbate 80. Pharmacoat 606™ with Chromakote™ is formed of hydroxypropylmethyl cellulose, water, xanthan gum, methyl paraben, propyl paraben, potassium sorbate, titanium dioxide and dyes.

Preferred coating systems include 1,2,3-propanetriol triacetate as the plasticizer, and hydroxypropylmethyl cellulose or OPADRY™ as the film former, water as the solvent, and ferric oxide and/or titanium oxide as the colorant.

Where the composition of the invention is to be in the form of a capsule, the capsule of the invention may optionally include a disintegrant and/or a flow aid as set out above.

A preferred tablet or capsule composition of the invention will include from about 5 to about 70% by weight sodium salt of infetroban, from about 1 to about 10% by weight magnesium oxide, from about 10 to about 80% by weight mannitol, from about 10 to about 80% by weight microcrystalline cellulose, from about 2 to about 8% by weight crospovidone and from about 0.5 to about 2% by weight magnesium stearate, and for the tablet from about 2 to about 4% by weight film coating which is OPADRY™ or hydroxypropylmethyl cellulose, and 1,2,3-propanetriol triacetate.

The pharmaceutical composition of the invention may be prepared by a direct compression manufacturing process as follows. A mixture of the medicament (preferably sodium salt of infetroban), basifying agent (preferably magnesium oxide), filler (such as mannitol and/or microcrystalline cellulose), binder (such as pregelatinized starch), disintegrant (such as crospovidone), with or without color, are mixed together and passed through a #12 to #40 mesh screen. Lubricant (such as magnesium stearate) is added with mixing until a homogeneous mixture is obtained.

The resulting mixture may then be compressed into tablets of up to 1 gram in weight or filled into hard gelatin capsules at up to 1 gram in weight.

Where desired, the composition of the invention may be formulated by a wet granulation technique wherein medicament (preferably, sodium salt of infetroban) is dissolved in water. The resulting solution is used to wet granulate a mixture of a fraction (less than 50%) or optionally the entire amount of the filler (such as mannitol and/or microcrystalline cellulose or others), basifying agent (such as magnesium oxide), and a fraction (less than about 50%) of disintegrant (such as croscarmellose sodium), and optional dry binder (such as pregelatinized starch). The granulated mixture is then dried in a tray drying oven (or by other means such as fluidized bed drying). The dried granulation is comminuted by a suitable means such as by passing through a #12 to #40 mesh screen. The remainder of the filler, disintegrant and the lubricant (such as magnesium stearate) are added and the resulting granules are compressed into tablets or filled into capsules.

The composition of the invention may also be formulated by a second wet granulation technique where a mixture of the medicament (preferably sodium salt of infetroban), basifying agent (preferably magnesium oxide), dry binder (such as pregelatinized starch), and a fraction (less than 50%) of the filler (such as mannitol) with or without color, are wet granulated with water or an aqueous binder (such as povidone, also referred to as polyvinyl pyrrolidone) solution. The granulation is then dried in a tray drying oven or by other means (such as fluidized bed drying). The dried granulation is passed through a #12 to #40 mesh screen. A portion of the disintegrant (such as croscarmellose sodium) and the remaining mannitol are added and mixed. The remainder of the filler, disintegrant and the lubricant (such as magnesium stearate) are added and the resulting granules are compressed into tablets or filled into capsules.

The composition of the invention may be prepared by a dry granulation process as follows. Medicament such as infetroban, sodium salt mixed with a portion of the filler (about 50%), basifying agent, dry binder, and a portion of each of the disintegrant and lubricant (about 50% of each). The mix is densified by forming large tablets (slugs) when using a tablet press or wafers when using a roller compactor. The tablets (slugs) or wafers are reduced by passing through a hammer mill or a suitable screening device equipped with a #12 to #40 mesh screen. The remainder of the filler, disintegrant and lubricant are added and the resulting mix are compressed into tablets or filled into capsules.

The so formed tablet cores may be film coated by dissolving or suspending the film coating ingredients in water and then spraying the coating solution on the tablet cores.

The following Examples represent preferred embodiments of the present invention. All temperatures are expressed in degrees Centigrade unless otherwise indicated and all mesh sizes are U.S. Standard ASTME.

EXAMPLE 1

A formulation containing the sodium salt of ifetroban, in the form of tablets, having the following composition, was prepared by the direct compression manufacturing process described hereinbefore.

| Ingredient | Percent by Weight |
| --- | --- |
| Na Salt of Ifetroban | 5.25 |
| Mannitol | 78.5 |
| Microcrystalline Cellulose | 10.0 |
| Crospovidone | 3.0 |
| Magnesium Oxide | 2.0 |
| Magnesium Stearate | 1.25 |

Na salt of ifetroban, magnesium oxide, mannitol, microcrystalline cellulose, and crospovidone were mixed together for 2 to 10 minutes employing a suitable mixer. The resulting mixture was passed through a #12 to #40 mesh size screen. Thereafter, magnesium stearate was added and mixing was continued for 1 to 3 minutes.

The resulting homogeneous mixture was then compressed into tablets each containing 5.25 mg, infetroban sodium salt.

A dispersion of the tablets in water had a pH of about 10.1.

Upon subjecting the so-formed 5.25 mg tablets to a dissolution study at 30° C. for 2 weeks, it was found that the Na salt of ifetroban had excellent dissolution properties and showed rapid and complete dissolution when tested using a USP dissolution apparatus.

The same tablets without basifying agent which had a pH of less than 7 in aqueous dispersion showed slow and incomplete dissolution when tested after storage for 2 weeks at 30° C.

EXAMPLE 2

A formulation containing the Na salt of ifetroban, in the form of tablets, having the following composition was prepared by a direct compression manufacturing process as described in Example 1

| Ingredient | Percent by Weight |
| --- | --- |
| Na Salt of Ifetroban | 5.25 |
| Mannitol | 60.75 |
| Microcrystalline Cellulose | 20.0 |
| Pregelatinized Starch | 10.0 |
| Magnesium Oxide | 2.0 |
| Sodium Stearyl Fumarate | 2.0 | except that pregelatinized starch and Na stearyl fumarate were employed in place of crospovidone and Mg stearate.

A dispersion of the tablets in water had a pH of about 10.

Upon subjecting the so-formed tablets to a dissolution study at 30° C. for 2 weeks, it was found that the tablets including the sodium salt of infetroban had excellent dissolution properties, and showed rapid and complete dissolution when tested using U.S.P. dissolution apparatus.

The same tablets without basifying agent, which had a pH of less than 7 in aqueous dispersion, showed slow and incomplete dissolution when tested after storage for 2 weeks at 30° C.

EXAMPLE 3

An ifetroban sodium salt formulation in the form of tablets, each containing about 1 mg ifetroban sodium salt, having the following composition was prepared by a wet granulation procedure as described hereinbefore.

| Ingredient | Percent by Weight |
| --- | --- |
| Na Salt of Ifetroban | 1.05 |
| Dicalcium Phosphate Dehydrate | 85.95 |
| Pregelatinized Starch | 10.0 |
| Magnesium Oxide | 2.0 |
| Magnesium Stearate | 1.0 |

A dispersion of the tablet in water had a pH of about 10.

Upon subjecting the so-formed tablets to a dissolution study at 30° C. for 2 weeks, it was found that the tablets, including the ifetroban sodium salt, showed rapid and complete dissolution when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 4

A ifetroban sodium salt formulation in the form of tablets, each containing 1.05 mg ifetroban sodium salt, having the following composition, was prepared by a wet granulation procedure as described hereinbefore.

| Ingredient | Percent by Weight |
|---|---|
| Na Salt of Ifetroban | 1.05 |
| Mannitol | 51.95 |
| Microcrystalline Cellulose | 31.0 |
| Pregelatinized Starch | 10.0 |
| Calcium Carbonate | 1.0 |
| Crospovidone | 4.0 |
| Magnesium Stearate | 1.0 |

A dispersion of the tablets in water had a pH of 10.

Upon subjecting the so-formed tablets to a dissolution study at 30° C. for 2 weeks, it was found that the tablets including the ifetroban showed rapid and complete dissolution properties when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 5

An ifetroban sodium salt formulation in the form of tablets, each containing 20 mg ifetroban sodium salt, having the following composition was prepared by the first wet granulation technique described hereinbefore.

| Ingredient | Percent by Weight |
|---|---|
| Na Salt of Ifetroban | 20.0 |
| Lactose | 45.0 |
| Starch | 20.0 |
| Aluminum Hydroxide | 10.0 |
| Povidone | 2.5 |
| Ferric Oxide | 0.5 |
| Magnesium Stearate | 1.5 |
| Colloidal Silicon Dioxide | 0.5 |

A dispersion of the tablets in water had a pH of about 10.

Upon subjecting the so-formed tablets to a dissolution study at 30° C. for 2 weeks, it was found that the tablets including the ifetroban sodium salt had rapid and complete dissolution properties when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 6

An ifetroban sodium salt formulation in the form of tablets, each containing about 10.5 mg ifetroban sodium salt, having the following composition, was prepared by a dry granulation technique as described hereinbefore.

| Ingredient | Percent by Weight |
|---|---|
| Na Salt of Ifetroban | 10.5 |
| Mannitol | 74.75 |
| Microcrystalline Cellulose | 10.0 |
| Crospovidone | 4.0 |
| Sodium Bicarbonate | 0.5 |
| Magnesium Stearate | 0.25 |

A dispersion of the tablets in water had a pH of about 8.

Upon subjecting the so-formed tablets to a dissolution study at 30° C. for 2 weeks, it was found that the tablets including the ifetroban sodium salt had excellent dissolution properties and showed rapid and complete dissolution when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 7

An ifetroban sodium salt formulation in the form of tablets, each containing 35 mg ifetroban sodium salt, having the following composition was prepared by a dry granulation technique as described hereinbefore.

| Ingredient | Percent by Weight |
|---|---|
| Na Salt of Ifetroban | 35.0 |
| Mannitol | 50.2 |
| Microcrystalline Cellulose | 8.0 |
| Crospovidone | 3.0 |
| Magnesium Oxide | 2.0 |
| Colloidal Silicon Dioxide | 0.3 |
| Magnesium Stearate | 1.5 |

A dispersion of the tablets in water had a pH of about 10.

Upon subjecting the so-formed tablets to a dissolution study at 30° C. for 2 weeks, it was found that the tablets including the ifetroban sodium salt showed rapid and complete dissolution properties when tested using a U.S.P. dissolution apparatus.

The same tablets without basifying agent which has a pH of less than 7 in aqueous dispersion showed slow and incomplete dissolution when tested after storage for 2 weeks at 30° C.

It will also be appreciated that capsules prepared in accordance with the present invention containing ifetroban salt, filler, basifying agent, lubricant and optionally disintegrant and/or flow aid will have excellent dissolution properties.

EXAMPLE 8

A film coated tablet containing 5.1 mg ifetroban sodium salt having the following composition was prepared as follows.

| Ingredient | Percent by Weight of Coated Tablet |
|---|---|
| Na Salt of Ifetroban | 5.1 |
| Mannitol | 76.2 |
| Microcrystalline Cellulose | 9.7 |

-continued

| | Percent by Weight of Coated Tablet |
|---|---|
| Crospovidone | 2.9 |
| Magnesium Oxide | 1.9 |
| Magnesium Stearate | 1.2 |
| Film Coating | |
| Hydroxypropylmethyl Cellulose | 1.7 |
| 1,2,3-Propanetriol Triacetate | 0.7 |
| Ferric Oxide | 0.3 |
| Titanium Dioxide | 0.3 |

The tablet core was prepared as described in Example 1.

The film coated tablets were prepared by dissolving or suspending the film coating ingredients in water and then spraying the coating solution on the core tablets.

A dispersion of the coated tablet in water had a pH of about 10.

Upon subjecting the so-formed tablets to a dissolution study at 30° C. for 2 weeks, it was found that the tablets, including the ifetroban sodium salt, showed rapid and complete dissolution when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 9

A film coated tablet containing 34 mg ifetroban sodium salt having the following composition was prepared as follows.

| | Percent by Weight of Coated Tablet |
|---|---|
| Ingredient | |
| Na Salt of Ifetroban | 34.0 |
| Mannitol | 48.7 |
| microcrystalline Cellulose | 7.8 |
| Crospovidone | 2.9 |
| Magnesium Oxide | 1.9 |
| Colloidal Silicon Dioxide | 0.3 |
| Magnesium Stearate | 1.2 |
| Film Coating | |
| OPADRY ™ | 3.2 |

The tablet core was prepared as described in Example 1.

The film coated tablets were prepared by dissolving or suspending the film coating ingredients in water and then spraying the coating solution on the core tablets.

A dispersion of the coated tablet in water had a pH of about 10.

Upon subjecting the so-formed tablets to a dissolution study at 30° C. for 2 weeks, it was found that the tablets, including the ifetroban sodium salt, showed rapid and complete dissolution when tested using a U.S.P. dissolution apparatus.

The same tablets without basifying agent which had a pH of less than 7 in aqueous dispersion showed slow and incomplete dissolution when tested after storage for 2 weeks at 30° C.

EXAMPLE 10

An ifetroban sodium salt formulation was prepared in the form of capsules, each containing 5.25 % by weight ifetroban sodium salt and magnesium oxide alkalizing agent, in accordance with the present invention, having the following composition.

| Example 10 Formulation (With MgO Alkalizing Agent) | |
|---|---|
| Ingredient | Percent by Weight |
| Na Salt of Ifetroban | 5.25 |
| Dicalcium Phosphate Dehydrate | 82.25 |
| Pregelatinized Starch | 10.0 |
| Magnesium Oxide | 2.0 |
| Magnesium Stearate | 0.5 |

A dispersion of the ingredients of the Example 10 capsule in water had a pH of about 9.8.

As a Control, the following ifetroban sodium salt formulation in the form of capsules was prepared, each containing 5.25 % by weight ifetroban, but containing no magnesium oxide alkalizing agent.

| Control Formulation (No MgO Alkalizing Agent) | |
|---|---|
| Ingredient | Percent by Weight |
| Na Salt of Ifetroban | 5.25 |
| Dicalcium Phosphate Dihydrate | 84.25 |
| Pregelatinized Starch | 10.0 |
| Magnesium Stearate | 0.5 |

A dispersion of the ingredients of the Control capsule in water had a pH of about 6.8.

The Example 10 capsules and Control capsules were stored at 30° C., and 40° C./75% RH, and the capsules were withdrawn at specified time intervals as indicated below.

Dissolution testing of the Example 10 capsules and Control capsules was performed using the following procedure.

The dissolution method employed USP Apparatus II (paddle) at 50 rpm in 900 mL distilled water heated to 37° C. Samples were taken at 10, 20, 30, 45, and 60 minutes. The sample was filtered through a 0.45 µm syringe filter, transferred to HPLC vials and analyzed by HPLC.

The following dissolution data was obtained for the Example 10 capsules and the Control capsules.

| | % Ifetroban Dissolved | | | | |
|---|---|---|---|---|---|
| | 10 min | 20 min | 30 min | 45 min | 60 min |
| Dissolution Data For Example 10 Formulation (With MgO Alkalizing Agent) | | | | | |
| Initial | 101 | 101 | 103 | 103 | 103* |
| 30° C./37 days | 101 | 102 | 102 | 103 | 103 |
| 40° C./75% RH, 37 days | 96 | 99 | 101 | 102 | 103 |
| Dissolution Data For Control Formulation** (No MgO Alkalizing Agent) | | | | | |
| Initial | 100 | 102 | 103 | 103 | 103 |
| 30° C./39 days | 63 | 76 | 84 | 88 | 92 |
| 40° C./75% RH, 30 days | 3 | 12 | 18 | 27 | 32 |

-continued

| | % Ifetroban Dissolved | | | | |
|---|---|---|---|---|---|
| | 10 min | 20 min | 30 min | 45 min | 60 min |

*The fact that the data shows slightly more than 100% dissolution in certain instances is due to assay variability.

**The Control formulation was stored at 40° C./75% RH and 30° C. This formulation was scheduled to be tested at 30 days interval for 40° C./75% RH and at 3 months interval for 30° C. condition. However, the unexpected dissolution slow down observed at the more accelerated condition (40° C./75% RH) prompted testing of 30° C. samples at earlier than scheduled time point. The results indicated that even at a more moderate condition (30° C.) this formulation show the dissolution slow down.

**The Control formulation was stored at 40° C./75% RH and 30° C. This formulation was scheduled to be tested at 30 days interval for 40° C./75% RH and at 3 months interval for 30° C. condition. However, the unexpected dissolution slow down observed at the more accelerated condition (40° C./75% RH) prompted testing of 30° C. samples at earlier than scheduled time point. The results indicated that even at a more moderate condition (30° C.) this formulation shows the dissolution slow down.

The above data shows that the ifetroban sodium salt capsules containing the MgO alkalizing agent (Example 10 formulation) underwent rapid and complete dissolution initially and after 37 days when tested using the USP Apparatus (II).

The same capsules without the MgO alkalizing agent showed slow and incomplete dissolution when tested initially, after 30 days and after 39 days.

EXAMPLE 11

An ifetroban sodium salt formulation was prepared in the form of capsules, each containing 10.5 mg ifetroban sodium salt and calcium carbonate alkalizing agent, in accordance with the present invention, having the following composition.

| Example 11 Capsule Formulation (with CaCO₃ Alkalizing Agent) | |
|---|---|
| Ingredient | Percent by Weight |
| Na Salt of Ifetroban | 5.25 |
| Mannitol | 77.00 |
| Microcrystalline Cellulose | 10.00 |
| Crospovidone | 3.00 |
| Calcium Carbonate | 4.00 |
| Magnesium Stearate | 0.75 |
| Capsule fill weight | 200.00 |

A dispersion of the ingredients of the Example 11 capsule in water had a pH of about 8.7.

The following ifetroban sodium salt formulation in the form of capsules was prepared, each containing 5.25 % by weight ifetroban, but containing no magnesium oxide alkalizing agent.

| Formulation Containing No Alkalizing Agent | |
|---|---|
| Ingredient | Percent by Weight |
| Na Salt of Ifetroban | 5.25 |
| Dicalcium Phosphate Dehydrate | 84.25 |
| Pregelatinized Starch | 10.00 |
| Magnesium Stearate | 0.50 |

A dispersion of the ingredients of the above capsule formulation in water had a pH of about 6.8.

The Example 11 capsules were stored at 30° C. for 2 years, and the capsules were withdrawn at specified time interval.

The capsules without the alkalizing agent were stored at 30° C. and 40° C./75% RH and were withdrawn at specified time intervals as indicated below.

Dissolution testing of the Example 11 capsules and the capsules without the alkalizing agent was performed using the following procedure.

The dissolution method employed USP Apparatus II (paddle) at 50 rpm in 900 mL distilled water heated to 37° C. Samples were taken at 10, 20, 30, 45, and 60 minutes. The sample was filtered through a 0.45 μm syringe filter, transferred to HPLC vials and analyzed by HPLC.

The following dissolution data was obtained for the Example 11 capsules and the capsules without the alkalizing agent.

| | % Ifetroban Dissolved | | | | |
|---|---|---|---|---|---|
| | 10 min | 20 min | 30 min | 45 min | 60 min |
| Dissolution Data For Example 11 Formulation (With CaCO₃ Alkalizing Agent) | | | | | |
| Initial | 96 | 99 | 99 | 100 | 100 |
| 30° C./2 years | 90 | 99 | 101 | 102 | 102* |
| Dissolution Data For Formulation** Without Alkalizing Agent | | | | | |
| Initial | 100 | 102 | 103 | 103 | 103* |
| 30° C./39 days | 63 | 76 | 84 | 88 | 92 |
| 40° C./75% RH, 30 days | 3 | 12 | 18 | 27 | 32 |

*The fact that the data shows slightly more than 100% dissolution in certain instances is due to assay variability.

**The formulation was stored at 40° C./75% RH and 30° C. This formulation was scheduled to be tested at 30 days interval for 40° C./75% RH and at 3 months interval for 30° C. condition. However, the unexpected dissolution slow down observed at the more accelerated condition (40° C./75% RH) prompted testing of 30° C. samples at earlier than scheduled time point. The results indicated that even at a more moderate condition (30° C.) this formulation shows dissolution slow down.

**The formulation was stored at 40° C./75% RH and 30° C. This formulation was scheduled to be tested at 30 days interval for 40° C./75% RH and at 3 months interval for 30° C. condition. However, the unexpected dissolution slow down observed at the more accelerated condition (40° C./75% RH) prompted testing of 30° C. samples at earlier than scheduled time point. The results indicated that even at a more moderate condition (30° C.) this formulation shows the dissolution slow down.

The above data shows that the ifetroban sodium salt capsules containing the CaCO₃ alkalizing agent (Example 11 formulation) underwent rapid and complete dissolution initially and after 2 years when tested using the USP Apparatus (II).

The formulation without the CaCO₃ alkalizing agent showed slow and incomplete dissolution when tested initially, after 30 days and after 39 days.

EXAMPLE 12

An ifetroban sodium salt formulation was prepared in the form of tablets, each containing 262.5 mg ifetroban sodium salt and magnesium oxide alkalizing agent, in accordance with the present invention, having the following composition.

| Example 12 Tablet Formulation (with MgO Alkalizing Agent) | |
|---|---|
| Ingredient | Percent by Weight |
| Ifetroban | 42.0 |

| Example 12 Tablet Formulation (with MgO Alkalizing Agent) | |
| --- | --- |
| Ingredient | Percent by Weight |
| Microcrystalline cellulose | 31.5 |
| Mannitol | 12.0 |
| Pregelatinized Starch | 9.0 |
| Crospovidone | 3.0 |
| Magnesium Oxide | 0.5 |
| Colloidal silicon dioxide | 0.5 |
| Magnesium Stearate | 1.5 |
| Tablet Weight | 625.0 mg |
| (tablets were coated with Opadry white to 3% weight gain) | |

A dispersion of the ingredients of the Example 12 tablet in water had a pH of about 9.8.

As a Control, the following ifetroban sodium salt formulation in the form of tablets was prepared, each containing 39.5 % by weight (52.5 mg) ifetroban, but containing no magnesium oxide alkalizing agent.

| Control Tablet Formulation (No MgO Alkalizing Agent) | |
| --- | --- |
| Ingredient | Percent by Weight |
| Na Salt of Ifetroban | 39.50 |
| Microcrystalline cellulose | 52.00 |
| Povidone | 4.00 |
| Sodium Starch Glycolate | 4.00 |
| Magnesium Stearate | 0.50 |
| Tablet weight | 133.00 mg |

A dispersion of the ingredients of the Control tablet in water had a pH of about 7.2.

The Example 12 tablets were stored at 30° C. for 3.5 months in capped bottles, and at 40° C./75% RH for 3.5 months in open containers, and the tablets were withdrawn at specified time intervals as indicated below.

The Control tablets were stored at 40° C./75% RH for 1 month in open containers and the tablets were withdrawn at specified time intervals as indicated below.

Dissolution testing of the Example 12 tablets and Control tablets was performed using the following procedure.

The dissolution method employed USP Apparatus II (paddle) at 50 rpm in 900 mL distilled water heated to 37° C. Samples were taken at 10, 20, 30, 45, and 60 minutes. The sample was filtered through a 0.45 μm syringe filter, transferred to HPLC vials and analyzed by HPLC.

The following dissolution data was obtained for the Example 12 tablets and the Control tablets.

| | % Ifetroban Dissolved | | | | |
| --- | --- | --- | --- | --- | --- |
| | 10 min | 20 min | 30 min | 45 min | 60 min |
| Dissolution Data For Example 12 Tablet Formulation (With MgO Alkalizing Agent) | | | | | |
| Initial | 34 | 67 | 86 | 95 | 98* |
| 30° C./3.5 months | 31 | 63 | 80 | 94 | 96* |
| 40° C./75% RH/ 3.5 months | 43 | 79 | 90 | 94 | 96* |
| Dissolution Data For Control Tablet Formulation (No MgO Alkalizing Agent) | | | | | |
| Initial | 50 | 75 | 92 | 97 | 99 |

| | % Ifetroban Dissolved | | | | |
| --- | --- | --- | --- | --- | --- |
| | 10 min | 20 min | 30 min | 45 min | 60 min |
| 40° C./75% RH, 1 month | 40 | 64 | 75 | 78 | 86 |

The above data shows that the ifetroban sodium salt tablets containing the MgO alkalizing agent (Example 12 formulation) underwent rapid and complete dissolution initially and after 3.5 months when tested using the USP Apparatus (II).

The Control tablets without the MgO alkalizing agent showed slow and incomplete dissolution when tested initially, after 1 month.

*The fact that the data shows slightly less than 100% dissolution in certain instances is due to assay variability.

EXAMPLE 13

An ifetroban sodium salt formulation was prepared in the form of tablets, each containing 262.5 mg ifetroban sodium salt and magnesium oxide alkalizing agent, in accordance with the present invention, having the following composition.

| Example 13 Formulation (With MgO Alkalizing Agent) | |
| --- | --- |
| Ingredient | Percent by Weight |
| Na Salt of Ifetroban | 42.00 |
| Microcrystalline cellulose | 47.50 |
| Hydroxypropylcellulose | 4.00 |
| Crospovidone | 4.00 |
| Colloidal silicon dioxide | 4.00 |
| Magnesium Oxide | 0.50 |
| Magnesium Stearate | 1.50 |
| Tablet weight | 625.00 mg |

Tablets were coated with Opadry white to 3% weight gain.

A dispersion of the ingredients of the Example 13 tablet in water had a pH of greater than 9.

As a Control, the following ifetroban sodium salt formulation in the form of tablets was prepared, each containing 39.5% by weight (52.5 mg) ifetroban, but containing no magnesium oxide alkalizing agent.

| Control Formulation (No MgO Alkalizing Agent) | |
| --- | --- |
| Ingredient | Percent by Weight |
| Na Salt of Ifetroban | 39.50 |
| Microcrystalline cellulose | 52.00 |
| Hydroxypropylcellulose | 4.00 |
| Crospovidone | 4.00 |
| Magnesium Stearate | 0.50 |
| Tablet Weight | 133.00 mg |

A dispersion of the ingredients of the Control tablet in water had a pH of about 7.1.

The Example 13 tablets were stored at 40° C./75% RH, and the tablets were withdrawn at specified time intervals as indicated below.

The Control tablets were stored at 40° C./75% RH, for 1 month in open containers and the tablets were withdrawn at specified time intervals as indicated below.

Dissolution testing of the Example 13 tablets and Control tablets was performed using the following procedure.

The dissolution method employed USP Apparatus II (paddle) at 50 rpm in 900 mL distilled water heated to 37° C. Samples were taken at 10, 20, 30, 45, and 60 minutes. The sample was filtered through a 0.45 μm syringe filter, transferred to HPLC vials and analyzed by HPLC.

The following dissolution data was obtained for the Example 13 tablets and the Control tablets.

| | % Ifetroban Dissolved | | | | |
|---|---|---|---|---|---|
| | 10 min | 20 min | 30 min | 45 min | 60 min |
| Dissolution Data For Example 13 Tablet Formulation (With MgO Alkalizing Agent) | | | | | |
| Initial | 24 | 60 | 88 | 104 | 105 |
| 40° C./75% RH, 1 month | 33 | 70 | 97 | 102 | 102 |
| Dissolution Data For Control Tablet Formulation (No MgO Alkalizing Agent) | | | | | |
| Initial | 40 | 69 | 88 | 94 | 97* |
| 40° C./75% RH, 1 month | 41 | 65 | 79 | 85 | 88 |

*The fact that the data shows slightly less than 100% dissolution in certain instances is due to assay variability.

*The fact that the data shows slightly less than 100% dissolution in certain instances is due to assay variability.

The above data shows that the ifetroban sodium salt tablets containing the MgO alkalizing agent (Example 13 formulation) underwent rapid and complete dissolution initially and after 1 month when tested using the USP Apparatus (II).

The Control tablets without the MgO alkalizing agent showed slow and incomplete dissolution when tested initially, after 1 month.

EXAMPLE 14

An ifetroban sodium salt formulation was prepared in the form of capsules, each containing 10.5 mg ifetroban sodium salt and sodium carbonate alkalizing agent, in accordance with the present invention, having the following composition.

| Example 14 Formulation (With NaHCO₃ Alkalizing Agent) | |
|---|---|
| Ingredient | Percent by Weight |
| Na Salt of Ifetroban | 10.50 |
| Microcrystalline cellulose | 10.00 |
| Mannitol | 74.75 |
| Crospovidone | 4.00 |
| Sodium Bicarbonate | 0.50 |
| Magnesium Stearate | 0.25 |
| Capsule Fill Weight | 100.00 |

A dispersion of the ingredients of the Example 10 capsule in water had a pH of about 8.3.

As a Control, the following ifetroban sodium salt formulation in the form of capsules was prepared, each containing 5.25% by weight ifetroban, but containing no sodium bicarbonate alkalizing agent.

| Formulation With No NaHCO₃ Alkalizing Agent | |
|---|---|
| Ingredient | Percent by Weight |
| Na Salt of Ifetroban | 5.25 |
| Dicalcium Phosphate Dehydrate | 84.25 |
| Pregelatinized Starch | 10.0 |
| Magnesium Stearate | 0.5 |

A dispersion of the ingredients of the above capsule in water had a pH of about 6.8.

The Example 14 capsules were stored at 40° C./75% RH for 23 days (open) and 50° C. for 14 days (capped), and the capsules were withdrawn at specified time intervals as indicated below.

The capsules without the alkalizing agent were stored at 30° C. and 40° C./75% RH and the capsules were withdrawn at specified time intervals as indicated below.

Dissolution testing of the Example 14 capsules and capsules without NaHCO₃ was performed using the following procedure.

The dissolution method employed USP Apparatus II (paddle) at 50 rpm in 900 mL distilled water heated to 37° C. Samples were taken at 10, 20, 30, 45, and 60 minutes. The sample was filtered through a 0.45 μm syringe filter, transferred to HPLC vials and analyzed by HPLC.

The following dissolution data was obtained for the Example 14 capsules and the capsules without NaHCO₃.

| | % Ifetroban Dissolved | | | | |
|---|---|---|---|---|---|
| | 10 min | 20 min | 30 min | 45 min | 60 min |
| Dissolution Data For Example 14 Formulation (With NaHCO₃ Alkalizing Agent) | | | | | |
| Initial | 86 | 90 | 91 | 91 | 91* |
| 23 days, 40° C./75% RH open | 83 | 88 | 89 | 90 | 90* |
| 2 weeks 50° C. (capped) | 86 | 90 | 91 | 91 | 91* |
| Dissolution Data For Formulation Without NaHCO₃** | | | | | |
| Initial | 100 | 102 | 103 | 103 | 103 |
| 30° C./39 days | 63 | 76 | 84 | 88 | 92 |
| 40° C./75% RH, 30 days | 3 | 12 | 18 | 27 | 32 |

*The low value is due to the variability in the content uniformity of the capsules.

**The formulation without NaHCO₃ was stored at 40° C./75% RH and 30° C. This formulation was scheduled to be tested at 30 days interval for 40° C./75% RH and at 3 months interval for 30° C. condition. However, the unexpected dissolution slow down observed at the more accelerated condition (40° C./75% RH) prompted testing of 30° C. samples at earlier than scheduled time point. The results indicated that even at a more moderate condition (30° C.) this formulation shows the dissolution slow down.

The above data shows that the ifetroban sodium salt capsules containing the NaHCO₃ alkalizing agent (Example 14 formulation) underwent rapid and complete dissolution initially and after 23 days at 40° C./75% RH and after 2 weeks at 50° C. using the USP Apparatus (II).

The capsules without the NaHCO₃ alkalizing agent showed slow and incomplete dissolution when tested initially, after 30 days and after 39 days.

It will be appreciated that where in the above working Examples, the fact that the data shows slightly more than 100% dissolution in certain instances is due to assay variability.

What is claimed is:

1. A pharmaceutical composition which has good dissolution properties even after aging, comprising a medicament which is a salt of ifetroban and one or more basifying agents to impart a desired pH of at least 7 to an aqueous dispersion of said composition.

2. The pharmaceutical composition as defined in claim 1 wherein the ifetroban salt is the sodium salt, potassium salt, calcium salt or magnesium salt.

3. The pharmaceutical composition as defined in claim 1 wherein said ifetroban salt is present in an amount within the range of from about 1 to about 60% by weight of the composition.

4. The pharmaceutical composition as defined in claim 1 wherein the medicament is ifetroban sodium salt.

5. The pharmaceutical composition as defined in claim 1 wherein the basifying agent is present in an amount within the range of from about 0.2 to about 75% by weight of the composition.

6. The pharmaceutical composition as defined in claim 1 wherein the basifying agent is an alkali metal hydroxide or salt, an alkaline earth metal hydroxide or salt or ammonium hydroxide.

7. The pharmaceutical composition as defined in claim 6 wherein the basifying agent is MgO, $Mg(OH)_2$, $Ca(OH)_2$, NaOH, KOH, LiOH, $NH_4OH$, $Al(OH)_3$, magaldrate, $CaCO_3$ or $NaHCO_3$.

8. The pharmaceutical composition as defined in claim 1 in the form of a tablet further including a filler present in an amount within the range of from about 5 to about 95% by weight.

9. The pharmaceutical composition as defined in claim 8 wherein the filler is lactose, sugar, corn starch, modified corn starch, mannitol, dicalcium phosphate dihydrate, maltodextrin, calcium sulfate, sorbitol, wood cellulose, microcrystalline cellulose, calcium carbonate or mixtures thereof.

10. The pharmaceutical composition as defined in claim 1 wherein a binder is optionally present in an amount within the range of from about 1 to about 35% by weight.

11. The pharmaceutical composition as defined in claim 10 wherein the binder is microcrystalline cellulose, povidone, corn starch, modified corn starch, hydroxypropylmethylcellulose, sugars, gum acacia, carnauba wax, paraffin, spermaceti, polyethylenes or microcrystalline wax.

12. The pharmaceutical composition as defined in claim 8 further including a disintegrant present in an amount within the range of from about 0.5 to about 10% by weight.

13. The pharmaceutical composition as defined in claim 12 wherein the disintegrant is croscarmellose sodium, crospovidone, sodium starch glycolate, pregelatinized starch, corn starch or microcrystalline cellulose.

14. The pharmaceutical composition as defined in claim 1 in the form of a tablet having the following formulation:

from about 5 to about 70% by weight ifetroban sodium salt;

from about 1 to about 10% by weight of basifying agent which is magnesium oxide, calcium carbonate, sodium bicarbonate or aluminum hydroxide, to impart a pH of at least 7;

further including from about 10 to about 90% by weight of a filler which is mannitol, microcrystalline cellulose, lactose, and/or dicalcium phosphate dihydrate;

optionally including from about 2 to about 20% by weight microcrystalline cellulose, starch and/or polyvinylpyrrolidone as a binder;

optionally including from about 2 to about 8% by weight of croscarmellose sodium or crospovidone as a disintegrant; and further including from about 0.5 to about 2% by weight magnesium stearate as a lubricant.

15. The pharmaceutical composition as defined in claim 1 having a pH in water of from 8 to 11.

16. The pharmaceutical composition as defined in claim 1 in the form of a tablet or capsule.

17. The pharmaceutical composition as defined in claim 1 in the form of a coated tablet which includes a film coating.

18. The pharmaceutical composition as defined in claim 1 wherein the film coating comprises up to about 15% by weight of the coated tablet and is formed of one or more film-formers or binders and a plasticizer.

19. The pharmaceutical composition as defined in claim 18 wherein the film-former is a hydrophilic polymer which is hydroxypropylmethyl cellulose, hydroxypropyl cellulose, sodium carboxymethyl cellulose or methylcellulose, and/or a hydrophobic polymer which is ethyl cellulose, cellulose acetate, polyvinyl-maleic anhydride polymer, acrylic acid polymer and the plasticizer is 1,2,3-propanetriol triacetate, triethyl citrate, tributyl citrate, diethyl phthalate, castor oil and/or polyethylene glycol.

20. A method of maintaining or improving dissolution properties of a salt of ifetroban on aging, which comprises including with an ifetroban salt composition one or more basifying agents, compatible with ifetroban salt, to impart a desired pH of a least 7 to an aqueous dispersion of the composition.

21. The method as claimed in claim 20 wherein said ifetroban salt is present in an amount within the range of from about 1 to about 60% by weight of the composition and the basifying agent is present in an amount within the range of from about 1 to about 75% by weight of the composition.

22. The method as defined in claim 20 wherein the basifying agent is an alkali metal hydroxide or salt, an alkaline earth metal hydroxide or salt or ammonium hydroxide.

* * * * *